US010542952B2

(12) United States Patent
Allmendinger et al.

(10) Patent No.: US 10,542,952 B2
(45) Date of Patent: Jan. 28, 2020

(54) SPECTRUM-NEUTRAL DETERMINATION OF CALCAREOUS DEPOSITS IN BLOOD VESSELS

(71) Applicant: Siemens Healthcare GmbH, Erlangen (DE)

(72) Inventors: Thomas Allmendinger, Forchheim (DE); Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 218 days.

(21) Appl. No.: 15/499,075

(22) Filed: Apr. 27, 2017

(65) Prior Publication Data
US 2017/0311917 A1    Nov. 2, 2017

(30) Foreign Application Priority Data
Apr. 29, 2016 (DE) .................. 10 2016 207 437

(51) Int. Cl.
*A61B 6/00* (2006.01)
*A61B 6/03* (2006.01)

(52) U.S. Cl.
CPC .......... *A61B 6/5217* (2013.01); *A61B 6/032* (2013.01); *A61B 6/461* (2013.01); *A61B 6/503* (2013.01); *A61B 6/5205* (2013.01); *A61B 6/583* (2013.01)

(58) Field of Classification Search
CPC .... A61K 2300/00; A61B 6/32; A61B 6/5217; A61B 6/032; A61B 6/461; A61B 6/503;
(Continued)

(56) References Cited

U.S. PATENT DOCUMENTS 6,674,834 B1 * 1/2004 Acharya ............... A61B 6/032
378/18
7,031,426 B2 * 4/2006 Iatrou et al. ....... A61B 5/02007
378/18
(Continued)

FOREIGN PATENT DOCUMENTS

DE    102008030552 A1    12/2009
DE    102015225395 A1    6/2017

OTHER PUBLICATIONS

McCollough Cynthia H. et al.: "Coronary Artery Calcium: A Muliinstitutional, Multimanufacturer International Standard for Quantification at Cardiac CT", in: Radiology, vol. 243, No. 2, May 2007, pp. 527-538, DOI:10.1148/radiol.2432050808.
(Continued)

*Primary Examiner* — Courtney D Thomas
(74) *Attorney, Agent, or Firm* — Harness, Dickey & Pierce, P.L.C.

(57) ABSTRACT

A method is described for the determination of a calcium score for a patient to be examined with the aid of a CT system. The method is used to define patient-specific CT-acquisition parameters. In addition, material parameters for a model method for the generation of synthetic image data for virtual CT-acquisition parameters are calibrated using phantom image data recorded with reference CT-acquisition parameters. A calcium score assigned to synthetic phantom image data corresponds to a calcium score determined with phantom image data recorded with reference CT-acquisition parameters. Next, CT-projection-measurement data is acquired for a region of interest using the patient-specific CT-acquisition parameters. The acquired CT-projection-measurement data is used to generate synthetic image data using the calibrated model method. Finally, a calcium score is determined using a standard method on the basis of the
(Continued)

synthetic image data. Also described is a calcium-score-determining device. Also described is a computed tomography system.

22 Claims, 6 Drawing Sheets

(58) Field of Classification Search
CPC ....... A61B 6/5205; A61B 6/583; A61B 6/504; G01N 33/6893; G01N 2800/32; G06T 7/0012
See application file for complete search history.

(56) References Cited

U.S. PATENT DOCUMENTS

| | | | |
|---|---|---|---|
| 9,872,662 B2 | 1/2018 | Raupach | |
| 2003/0095693 A1* | 5/2003 | Kaufman | G06F 19/321 382/128 |
| 2004/0017936 A1* | 1/2004 | Gopinath | G06T 7/0012 382/131 |
| 2010/0014737 A1 | 1/2010 | Ruhrnschopf et al. | |
| 2015/0139517 A1 | 5/2015 | Sigurdsson | |
| 2017/0172533 A1 | 6/2017 | Raupach | |

OTHER PUBLICATIONS

Williamson, Jeffrey F. et al.: "On two-parameter models of photon cross sections: Application to dual-energy CT imaging", in: Med. Phys., vol. 33, No. 11, Nov. 2006, pp. 4115-4129, DOI:10.1118/1.2349688.

Alvarez, Robert E. et al.: Energy-selective Reconstructions in X-ray Computerized Tomography, Phys. Med. Biol., 1976, vol. 21, No. 5, pp. 733-744.

German Office Action #10 2016 207 437.7 dated Jan. 3, 2017.

* cited by examiner

SPECTRUM-NEUTRAL DETERMINATION OF CALCAREOUS DEPOSITS IN BLOOD VESSELS

PRIORITY STATEMENT

The present application hereby claims priority under 35 U.S.C. § 119 to German patent application number DE 102016207437.7 filed Apr. 29, 2016, the entire contents of which are hereby incorporated herein by reference.

FIELD

At least one embodiment of the invention generally relates to a method for the determination of a calcium score for a patient to be examined with the aid of a CT system. In addition, at least one embodiment of the invention generally relates a calcium-score-determining device. Finally, the invention relates to a computed tomography system.

BACKGROUND

Modern imaging methods are frequently used to generate two- or three-dimensional image data that can be used visualize an imaged object under examination and in addition to this also for further applications.

Imaging methods are frequently based on the acquisition of X-rays wherein so-called projection-measurement data is generated. For example, projection-measurement data can be acquired with the aid of a computed tomography system (CT system). Typically with CT systems, a combination of an X-ray source and an oppositely disposed X-ray detector arranged on a gantry rotates about a scanning chamber in which the object under examination (hereinafter, called the patient without restricting the generality) is located. In this context, the center of rotation (also called the "isocenter") coincides with a so-called system axis z. The patient is irradiated with X-rays from the X-ray source in the course of one or more rotations, wherein the oppositely disposed X-ray detector acquires projection-measurement data or X-ray projection data.

The X-ray detectors used in CT imaging usually comprise a plurality of detection units, which are generally arranged in the form of a regular pixel array. The detection units each generate a detection signal for X-rays striking the detection units said signal being analyzed at defined time points with respect to the intensity and spectral distribution of the X-rays in order to obtain information on the object under examination and generate projection-measurement data.

One field of application of computed tomography is the examination of coronary vessels. With coronary CT-angiography, the patient is first given a contrast medium. This is following by a depiction of the coronary vessels. The images can be used to determine the condition of the coronary vessels, wherein it is possible to check whether a patient is at risk of myocardial infarction or not. However, the administration of contrast media and the irradiation of the patient with X-rays are stressful. In particular, the administration of contrast media can be contraindicated in the case of restricted renal function.

A further method for examining the coronary vessels is known as calcium scoring. With this method, a CT image is taken without the use of a contrast medium and with low radiation exposure. On the basis of the density of the calcification, the calcium content of the coronary vessels is rated on a scale, the so-called Agatston score, and assigned to one of four categories (0-10; 10-100; 100-400; >400). The level of the calcium content is an indicator of the probability of myocardial infarction or at least angina pectoris developing within the next few years. Therefore, from a statistical viewpoint, a calcium content of 0-10 means that there is a low risk of the patient suffering myocardial infarction in the next five years. On the other hand, a calcium content of more than 400 means that the patient is at increased risk of myocardial infarction.

If the Agatston score is more than 500-600, it may be advisable additionally to perform a CT angiography scan in order to obtain a more accurate picture of the condition of the coronary vessels. The classification of such values relating to the calcium content with respect to reference values requires the observance of rigidly prespecified CT-acquisition parameters, in particular in respect of the required X-ray spectrum or the electric X-ray tube voltage correlated therewith. However, even the choice of standardized parameters does not eliminate certain uncertainties with the classification since different types of prefiltering with different CT systems means relatively high fluctuations or tolerance are to be expected (typically 6% for the Agatston score and 8% for the volume score).

In addition, the definition of the spectrum (corresponding to a tube voltage of 120 kV) for example for the Agatston score is based on historical factors. This value is related to the limited power reserves of an electron beam CT system, but is in no way ideal with respect to the dose efficiency of the calcium depiction. Low-energy spectra are much more efficient, but change the value of the Agatston score significantly and hence impede comparability with reference values.

For the determination of the Agatston score, a region to be depicted is divided into three-millimeter-thick image slices to be depicted. In each of the image slices, calcification is determined in that account is taken of regions with attenuation values of more than 130 HU. However, in this case, regions with an area of less than 1 mm$^2$ are ignored in order to suppress image noise. Each level of calcification detected is assigned to a region designated an ROI (region of interest) and a maximum attenuation value $CT_{max}$ is determined in the respective region. Then, each of the regions is assigned a weighting factor $w_i$, which is a function of the maximum attenuation value $CT_{max}$ determined. The weighting factor $w_i$ for each region $ROI_i$ is calculated as follows:

$$w_i = \begin{cases} 1, & \text{if } 130HU \leq CT_{max} \leq 200HU \\ 2, & \text{if } 200HU \leq CT_{max} \leq 300HU \\ 3, & \text{if } 300HU \leq CT_{max} \leq 400HU \\ 4, & \text{if } 400HU \leq CT_{max} \end{cases} \quad (1)$$

The calcium score $CS_i$ assigned to a region $ROI_i$ is then obtained as $$SC_i = w_i \cdot A_i, \quad (2)$$

wherein $A_i$ identifies the area of the respective region $ROI_i$.

It is also possible for a total value CS, hereinafter a value called the Agatston score, to be determined from the respective calcium score $CS_i$ as follows:

$$CS = \sum_i CS_i. \quad (3)$$

A further value used for the Ca scoring is the so-called volume score. The volume score provides information regarding the calcification volume. For the determination of the volume score, the number of voxels exceeding a threshold value is multiplied by the respective voxel volume, wherein a technique of isotropic interpolation is used. Here, the threshold value used is preferably a value of 130 HU.

Another value used for the calcium scoring is the so-called mass score. The mass score provides information on the total mass of the calcification identified.

When reference is made to the determination of a calcium score is the following, this term covers the above-named parameters: Agatston score, volume score and mass score.

It would be desirable to adapt the protocol parameters for a CT image for the determination of a calcium score in deviation from the defined standard parameters, for example an X-ray tube voltage of 120 kV, to the respective requirements with respect to image quality or dose reduction.

SUMMARY

Therefore, the inventors have realized that there is a problem relating to improving the concept of the application of calcium scores so that it is more flexible and reliable to use.

Embodiments of the present application are directed to a method for the determination of a calcium score; a calcium-score-determining device; and a computed tomography system.

The method for the determination of a calcium score of at least one embodiment determines a calcium score for a patient to be examined with the aid of a CT system. In this context, patient-specific CT-acquisition parameters are defined. Therefore, unlike conventional methods for the determination of a calcium score, this does not make use of the default acquisition-parameter values specified, instead there is a deliberate deviation from these standard values in order to increase image quality and dose efficiency and hence also to reduce the dose to which the patient is exposed. CT-acquisition parameters comprise, for example, the tube voltage of an X-ray tube or X-ray source used for CT imaging and also prefiltering of the X-rays emitted and the physical dimensions of a patient or parameters to be derived therefrom. Such parameters influence the spectral distribution of the X-rays emitted onto an object to be examined or transmitted thereby.

The calcium-score-determining device according to at least one embodiment of the invention is for the determination of a calcium score for a patient to be examined with the aid of a CT system comprises a parameter-defining unit for the definition of patient-specific CT-acquisition parameters.

The computed tomography system according to at least one embodiment of the invention comprises a scanning unit for acquiring a region of interest of an object under examination and a controller for controlling the scanning unit. The computed tomography system according to at least one embodiment of the invention also comprises a calcium-score-determining device according to at least one embodiment of the invention.

An extensively software-based implementation has the advantage that it is also simple to retrofit previously used control device for CT systems with said calcium-score-determining device by way of a software update in order to employ the method according to at least one embodiment of the invention.

A corresponding computer program product is also disclosed with a computer program, which can be loaded directly in a storage device of a control device of computer tomography system, with program sections in order to carry out all the steps of the method according to at least one embodiment of the invention when the program is executed in the control device. In addition to the computer program, such a computer program product can optionally also comprise additional components, such as, for example documentation and/or additional components and also hardware components, such as for example hardware keys (dongles etc.) in order to use the software.

It possible for a computer-readable medium to be used for transportation to the control device and/or for storage on or in the control device, for example a memory stick, a hard disk or another type of transportable or permanently installed data medium on which the program sections of the computer programs that can be read and executed by a computing unit of the control device are stored. To this end, the computing unit can, for example, comprise one or a more interacting microprocessors or the like.

The claims and the following description each contain particularly advantageous embodiments and developments of the invention. In this context, it is in particular also possible to develop the claims of one claim category similarly to the dependent claims of another claim category. In addition, in the context of the invention, it is also possible to combine the different features of different example embodiments and claims to form new example embodiments.

BRIEF DESCRIPTION OF THE DRAWINGS

The invention is described again in more detail below with reference to the attached figures and to example embodiments. The drawing shows.

DETAILED DESCRIPTION OF THE EXAMPLE EMBODIMENTS

Figure 1:
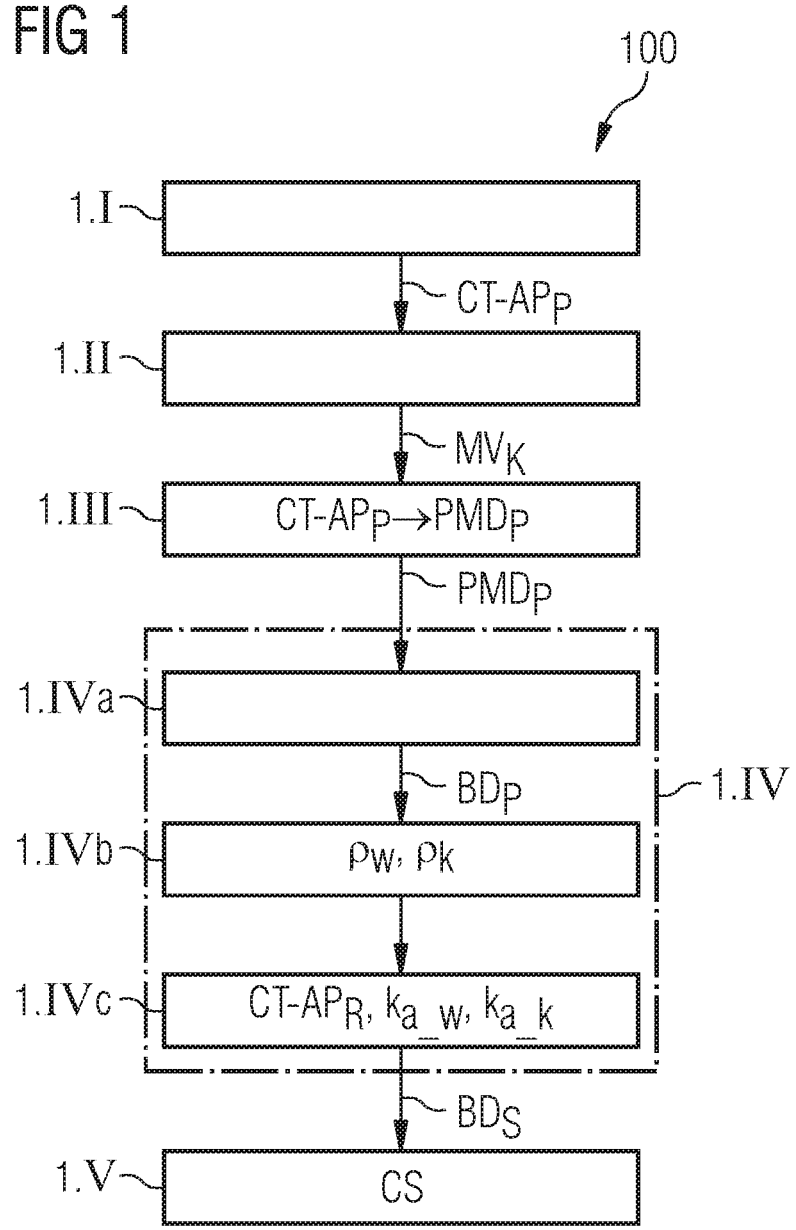
FIG. 1 a flow diagram illustrating a method for the determination of a calcium score for a patient to be examined with a CT system, FIG. 2 a flow diagram elucidating a calibration process within the context of the method illustrated in FIG. 1, FIG. 3 a calcium-score-determining device according to one example embodiment of the invention, FIG. 4 a graph illustrating a variation of the values of a conventionally-determined Agatston score in dependence on values of the X-ray tube voltage, the prefiltering of the X-rays and the dimensions of the patient, FIG. 5 a graph illustrating a variation of the values of an Agatston score determined with the method according to the invention in dependence on values of the X-ray tube voltage used, the prefiltering of the X-rays and the dimensions of the patient, FIG. 6 a computed tomography system according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method for the determination of a calcium score of at least one embodiment determines a calcium score for a patient to be examined with the aid of a CT system. In this context, patient-specific CT-acquisition parameters are defined. Therefore, unlike conventional methods for the determination of a calcium score, this does not make use of the default acquisition-parameter values specified, instead there is a deliberate deviation from these standard values in order to increase image quality and dose efficiency and hence also to reduce the dose to which the patient is exposed. CT-acquisition parameters comprise, for example, the tube voltage of an X-ray tube or X-ray source used for CT imaging and also prefiltering of the X-rays emitted and the physical dimensions of a patient or parameters to be derived therefrom. Such parameters influence the spectral distribution of the X-rays emitted onto an object to be examined or transmitted thereby.

Moreover, material parameters for a model method used for the generation of synthetic image data for virtual CT-acquisition parameters are calibrated in at least one embodiment. Material parameters can, for example, comprise absorption coefficients of different types of material, in particular as a function of the energy of the X-rays emitted.

The calibration is performed using phantom image data recorded with reference CT-acquisition-parameter values. These reference CT-acquisition-parameter values are also called standard CT-acquisition-parameter values and are usually permanently prespecified for the determination of a specific calcium score. During the determination of the Agatston Scores, an X-ray tube voltage of 120 kV is, for example, specified as a standard CT-acquisition-parameter value. The calibration is performed such that a calcium score determined on the basis of synthetic phantom image data corresponds to a calcium score determined on the basis of the phantom image data recorded with reference CT-acquisition parameters.

This adaptation of the synthetic image data takes place by changing the material parameters named, which are selected such that a calcium score determined on the basis of the synthetic image data is as close as possible to the calcium score determined under standard conditions. In this context, synthetic image data should be understood to be image data calculated on the basis of image data recorded with other acquisition-parameter values. In this context, the synthetic image data is determined such that it corresponds to image data recorded with the reference CT-acquisition parameters. However, since inaccuracies generally occur with a model-based calculation of the synthetic image data, without a calibration of the model method for generating the synthetic image data on the basis of image data recorded with patient-specific acquisition parameters, the value determined for a calcium score would deviate from a calcium score determined under standard conditions or with the aid of direct CT imaging with reference CT-acquisition parameters. In order to reduce this deviation, the calibration described is performed with the aid of the phantom image data.

In this context, a phantom or calibration phantom is intended to designate an object used for the calibration of the CT system. The phantom in particular comprises calcium or calcium compounds as test material in predetermined quantities and concentration in predetermined ranges.

This is followed by the actual CT imaging of the patient on the basis of which the individual calcium score of the patient to be examined is then to be determined. In this context, CT-projection-measurement data is acquired for a region of interest, preferably comprising the heart region of the patient using the patient-specific CT-acquisition parameters. On the basis of the acquired CT-projection-measurement data, following appropriate interim steps, synthetic image data is then generated using the model method adapted with the calibrated material parameters. Finally a calcium score is determined, for example using a standard method, on the basis of the reconstructed synthetic image data for the region of interest. Hence, a standard method of this kind is carried out in the same way as it would be carried out when using the reference or standard acquisition parameters so that advantageously no changes have to be made during the actual scoring process, such as, for example, the adaptation of threshold values. The method according to the invention removes any connection to the use of standard CT-acquisition parameters during CT imaging for the determination of a calcium score of a patient. I.e., it is possible to use patient-specific CT-acquisition parameters and nevertheless to determine a calcium score corresponding to the standard conditions. In addition to the afore-mentioned advantages of dose efficiency and lower dose exposure, this also achieves more independence of the calcium score from prefiltering and patient habitus.

In addition to the actual use with calcification, said calibration phantom can, for example, also comprise three "fat rings", which can be superimposed. It is, therefore, possible also to include measurements with different diameters and hence also take account of the dependence in the calibration.

However, the following applies in principle: the method described is derived from a correction to beam hardening. Therefore, on the basis of simulation, it recognizes the effect of the hardening of polychromatic radiation and hence generates a monochromatic response even without subsequent calibration. Therefore, with this method, independence of the score from the degree of 'fatness' is expected even without calibration and, in this case, the phantom measurement is used for an additional check.

A further advantage resides in the fact that, with dynamic CT imaging, the CT-acquisition parameters are selected such that the greatest possible temporal resolution is achieved. Such a procedure can also be combined with reconstruction methods which use algorithms to improve the temporal resolution in the sense that the temporal resolution is better than rotation time/2 or rotation time/4 with dual-source CT imaging.

The calcium-score-determining device according to at least one embodiment of the invention is for the determination of a calcium score for a patient to be examined with the aid of a CT system comprises a parameter-defining unit for the definition of patient-specific CT-acquisition parameters.

In addition, the calcium-score-determining device according to at least one embodiment of the invention comprises a calibration unit for the calibration of material parameters for a model method used for the generation of synthetic image data for virtual CT-acquisition parameters. The calibration unit performs the calibration using phantom image data recorded with reference CT-acquisition parameters such that a calcium score determined on the basis of synthetic phantom image data corresponds to a calcium score determined on the basis of the phantom image data recorded with reference CT-acquisition parameters.

The calcium-score-determining device according to at least one embodiment of the invention also comprises an acquisition-control-signal-generating unit for the generation of control signals for the acquisition of CT-projection-measurement data for a region of interest preferably comprising the heart region of the patient using the patient-specific CT-acquisition parameters.

In addition, the calcium-score-determining device according to at least one embodiment of the invention comprises a synthesis unit for the generation of synthetic image data on the basis of the acquired CT-projection-measurement data using the model method adapted with the calibrated material parameters.

The calcium-score-determining device according to at least one embodiment of the invention also comprises a calcium score-determining unit for determining the calcium score on the basis of the reconstructed synthetic image data.

A model method in the context of the generation of synthetic image data should be understood to be a method with which on the basis of prespecified image data, which is obtained, for example, by CT imaging with predetermined CT-acquisition parameters, synthetic image data for other desired virtual CT-acquisition parameters is generated. I.e. the synthetic image data is generated from the available image data by calculation.

For example, so-called dual-energy image data or generally multi-energy image data comprising two image data sets or generally a plurality of image data sets obtained with X-rays with different X-ray energy spectra can be used to calculate synthetic image data for a desired virtual X-ray energy spectrum. Such a model method is for example illustrated in DE 10 2008 030 552 A1, the entire contents of which are hereby incorporated herein by reference.

In the context of such a method, first, segmentation is performed according to portions in the examination region to which different absorption coefficients are to be assigned. For example, basic material can be segmented into two basic materials, such as, for example, soft tissue and calcium to each of which different absorption coefficients are assigned. Alternatively, it is also possible to perform segmentation according to portions of the photo effect and the Compton effect or a so-called ρ-Z segmentation with which segmentation is performed according to density and the effective ordinal number. This can be followed by the calculation of absorption coefficients for the desired virtual CT-acquisition parameters, in particular a virtual X-ray energy spectrum and, with knowledge of the portions from the segmentation, the calculation of attenuation values for the desired virtual CT-acquisition parameters.

At this point, express mention is made of the fact that the term 'model method' is intended to comprise not only image-data-synthesis methods based on dual-energy approaches or multi-energy approaches but also methods for the generation of synthetic image data on the basis of only one single image data set for one energy value or, viewed generally, for a set of CT-acquisition parameters, such as is described for example, in DE 10 2015 225 395.3, the entire contents of which are hereby incorporated herein by reference.

The computed tomography system according to at least one embodiment of the invention comprises a scanning unit for acquiring a region of interest of an object under examination and a controller for controlling the scanning unit. The computed tomography system according to at least one embodiment of the invention also comprises a calcium-score-determining device according to at least one embodiment of the invention.

The implementation of at least one embodiment of the invention in a CT system has the advantages that the scan duration of a CT system is relatively short. In contrast to recording with MRI systems, which can require several minutes, this only takes a few seconds. This is particularly advantageous when examining emergency patients for which any time delay can be life-threatening. In addition, CT systems are more widely used and less expensive than MRI systems.

The essential components of the calcium-score-determining device according to at least one embodiment of the invention can be predominantly embodied in the form of software components. This in particular relates to the parameter-defining unit, the calibration unit, the acquisition-control-signal-generating unit, the synthesis unit and the calcium score-determining unit. However, in principle, in particular when particularly quick calculations are required, these components can also be partially implemented in the form of software-supported hardware, for example FPGAs or the like. Similarly, for example when it is only a question of the acceptance of data from other software components, the interfaces required can be embodied as software interfaces. However, they can also be embodied as hardware-based interfaces controlled by suitable software.

An extensively software-based implementation has the advantage that it is also simple to retrofit previously used control device for CT systems with said calcium-scoredetermining device by way of a software update in order to employ the method according to at least one embodiment of the invention.

A corresponding computer program product is also disclosed with a computer program, which can be loaded directly in a storage device of a control device of computer tomography system, with program sections in order to carry out all the steps of the method according to at least one embodiment of the invention when the program is executed in the control device. In addition to the computer program, such a computer program product can optionally also comprise additional components, such as, for example documentation and/or additional components and also hardware components, such as for example hardware keys (dongles etc.) in order to use the software.

It possible for a computer-readable medium to be used for transportation to the control device and/or for storage on or in the control device, for example a memory stick, a hard disk or another type of transportable or permanently installed data medium on which the program sections of the computer programs that can be read and executed by a computing unit of the control device are stored. To this end, the computing unit can, for example, comprise one or a more interacting microprocessors or the like.

The claims and the following description each contain particularly advantageous embodiments and developments of the invention. In this context, it is in particular also possible to develop the claims of one claim category similarly to the dependent claims of another claim category. In addition, in the context of the invention, it is also possible to combine the different features of different example embodiments and claims to form new example embodiments.

Particularly preferably, with the method according to an embodiment of the invention, the generation of synthetic image data using the adapted model method comprises:
  reconstruction of image data on the basis of the X-ray projection-measurement data acquired using the patient-specific CT-acquisition parameters,
  segmentation of the image data according to material properties,
  determination of synthetic image data for the reference CT-acquisition parameters on the basis of the segmentation.

As already mentioned, a model method should be understood to be a calculation method for the generation of synthetic image data. As also addressed briefly above, this model method includes the segmentation of one or more image data sets according to the portions in the examination region to which different absorption coefficients are to be assigned.

In one embodiment of the method according to the invention, the patient-specific CT-acquisition parameters are defined taking account of the dose efficiency for the depiction of the calcium-soft tissue contrast. The freedom with respect to the choice of the CT-acquisition parameters means that, following an improvement to the dose efficiency, the patient's dose can be reduced so that a patient is exposed to less stress.

Improved dose efficiency can in particular be achieved if an X-ray tube voltage assigned to a patient-specific X-ray energy spectrum is defined as a patient-specific CT-acquisition parameter. For example, it is possible to use specific patient dimensions or other information on the condition of the patient's body in order to achieve an optimum choice of the X-ray tube voltage.

The patient-specific X-ray energy spectrum is preferably selected such that a desired dose efficiency for the depiction of the calcium-soft tissue contrast is achieved. Since, during the determination of a calcium score, in particular the calcification should be clearly identifiable in order to obtain the most accurate result possible, improved calcium-soft tissue contrast is particularly advantageous in CT imaging.

It is also preferable with the method according to an embodiment of the invention for the patient-specific X-ray energy spectrum to be defined in dependence on the dimensions, preferably a diameter of the patient and/or an attenuation of X-rays in the patient. In particular, when recording moving objects, such as, for example, the human heart, with 'fat' patients, the X-ray tube power achieved with low tube voltages is often no longer sufficient to carry out sufficient precise imaging. In such a case, therefore, higher X-ray tube voltages would be selected than for thin patients.

The patient-specific CT-acquisition parameters can, for example, comprise a patient-specific X-ray energy spectrum and the reference CT-acquisition parameters can comprise a reference X-ray energy spectrum. Therefore, instead of or additionally to the X-ray tube voltage, the patient-specific X-ray energy spectrum can be defined as a CT-acquisition parameter. For example, in addition to the X-ray tube energy, an X-ray energy spectrum can be influenced by further influencing variables, such as, for example, the type or properties of an additional prefilter.

The synthetic image data can, for example, comprise monoenergetic image data. I.e. image data to which a discrete X-ray spectrum is virtually assigned comprising only one energy value. The calculation of synthetic image data for individual energy values is particularly simple, since with the calculation of energy-dependent absorption coefficients, integration over energy is not necessary.

In one variant of the method according to an embodiment of the invention, the segmentation according to material properties comprises one of the following methods:
  basic material segmentation,
  photo/Compton effect segmentation,
  density-charge number segmentation.

Particularly suitable for the calculation of a calcium score is basic material segmentation according to the materials soft tissue and calcium. During the calibration of the material parameters, i.e. the absorption coefficients, it is then only necessary to adapt the absorption coefficient for calcium.

In one particularly preferred variant of the method according to an embodiment of the invention, the material parameters to be defined during the calibration step comprise the absorption coefficients of the basic materials.

In one particularly practicable variant of the method according to an embodiment of the invention, in the case of the determination of synthetic monoenergetic image data, in the calibration step, the absorption coefficients of the basic materials at the X-ray energy corresponding to the standard acquisition parameters are defined such that a calcium score determined at an X-ray energy corresponding to the patient-specific acquisition parameters corresponds to the calcium score determined with standard CT-acquisition parameters. This ensures that a determination of a calcium score with patient-specific acquisition parameters is also comparable with the standard determination of such a value.

With the method according to an embodiment of the invention, the calibration step is preferably performed with the aid of phantom image data generated by displaying a reference phantom with a known calcium score or by displaying an anthropomorphic phantom and/or by taking account of patient data. If an anthropomorphic phantom is used, the reference calcium score can be determined by an additional CT recording.

FIG. 1 shows a flow diagram 100 illustrating a method for the determination of a calcium score for a patient to be examined with a CT system according to one example embodiment of the invention. First, patient-specific CT-acquisition parameters CT-APP are defined in Step 1.I. These CT-acquisition parameters CT-APP can, for example, comprise the X-ray tube voltage with which a region of interest is scanned during CT imaging and which influences the energy spectrum of the X-rays used. The CT-acquisition parameters CT-APP can also comprise a parameter of a specific prefilter with which the X-rays are filtered before they penetrate the region of interest and which also influences the X-ray energy spectrum of the X-rays. The recording conditions or acquisition parameters in such a specific example embodiment would be typically defined as follows: an ECG-triggered spiral or sequential acquisition would be used. The spectrum should (for historical reasons) correspond to 130 kV, and if this is not available, 120 kV is used. In addition, an X-ray current is set that corresponds to approximately 25% of a contrast CT. It is sufficient to make the acquisition during one cardiac phase, typically in the end diastole. Hence, this procedure results in typical dose values of 1-4 mSv for this type of examination. Reducing the voltage to 70 kV, 80 kV, 90 kV, . . . , 100 kV would be combined with an adaptation of the current so that the calcium contrast is retained in a first approximation. I.e., the low voltage causes the attenuation values (HU values) of the calcium to rise thus enabling higher noise to be accepted since the signal-noise ratio is retained. As a result, a reduction in the dose of between 10% and 70% is to be expected. The actually possible voltage is individually dependent upon the power of the CT device and the patient's diameter.

In Step 1.II, before the actual imaging of the patient or a region of interest in the patient, a calibration method is performed with which a model method or the material parameters used in this context are adapted. In this calibration method, material parameters, in this specific example embodiment absorption coefficients for the material calcium, are calibrated. These calibrated absorption coefficients are to be used later within the context of a calibrated model method $MV_K$ during the determination of a calcium score on the basis of image data generated with patient-specific CT-acquisition parameters to generate synthetic image data. The adaptation of these material parameters is performed by way of a comparison with phantom images on the basis of which two calcium scores are calculated and compared. The comparison is performed such that a calcium score determined on the basis of synthetic image data of a reference phantom calculated from imaged data generated with patient-specific CT-acquisition parameters is compared with the value of a calcium score determined on the basis of image data of the reference phantom generated with reference CT-acquisition parameters. The calibration process in Step 1.II is depicted in detail in FIG. 2.

When the model method $MV_k$ has been calibrated in Step 1.III the actual CT imaging of a region of interest is performed with the patient-specific CT-acquisition parameters CT-AP$_P$ defined in Step 1.I. In this context, projection-measurement data PMD$_P$ is acquired from the region of interest.

This is followed in Step 1.IV by the use of projection-measurement data PMD$_P$ acquired to generate synthetic image data BD$_S$ to which virtual CT-acquisition parameters are assigned corresponding to the standard or reference CT-acquisition parameters CT-AP$_R$ with which a calcium score is usually determined. To this end, in Substep 1.IVa, first, image data BD$_P$ is reconstructed on the basis of the projection-measurement data PMD$_P$ of the region of interest of the patient acquired with the patient-specific CT-acquisition parameters CT-AP$_P$. This reconstruction can be performed with generally known methods, for example methods comprising filtered back projection. With the example embodiment shown in FIG. 1, the reconstructed image data BD$_P$ is then segmented into basic materials in Substep 1.IVb. In the case of the example embodiment shown in FIG. 1, the patient's heart is to be depicted. In this case, it is advisable to perform basic material segmentation into the materials soft tissue and calcium.

On the basis of the reconstructed image data BD$_P$ and the absorption coefficients $k_{a\_w}$, $k_{a\_k}$ for soft tissue and calcium calculated for the patient-specific CT-acquisition parameters CT-AP$_P$, it is possible to calculate location-dependent density values $\rho_w$, $\rho_k$ for the two basic materials which indicate the proportional contents of the materials in question in a respective voxel. Then, in Step 1.IVc, the calibrated absorption coefficients $k_{a\_k}$ determined in Step 1.II for calcium and the absorption coefficients $k_{a\_w}$ for soft tissue (this absorption coefficient $k_{a\_w}$ for soft tissue does not usually change during the calibration) are used for the determination of synthetic image data BD$_S$, which is assigned to the reference CT-acquisition parameters CT-AP$_R$. Unlike the use of an absorption coefficient $k_{a\_k}$ for calcium calculated directly on the basis of the reference CT-acquisition parameters CT-AP$_R$, the determination of the synthetic image data BD$_S$ is performed using an absorption coefficient $k_{a\_k}$ for calcium obtained by calibration in Step 1.II, which is matched to the correct determination of a calcium score CS. Finally in Step 1.V, a calcium score CS is calculated, for example an Agatston score, on the basis of the synthetic image data BD$_S$ determined in Step 1.IV.

Figure 2:
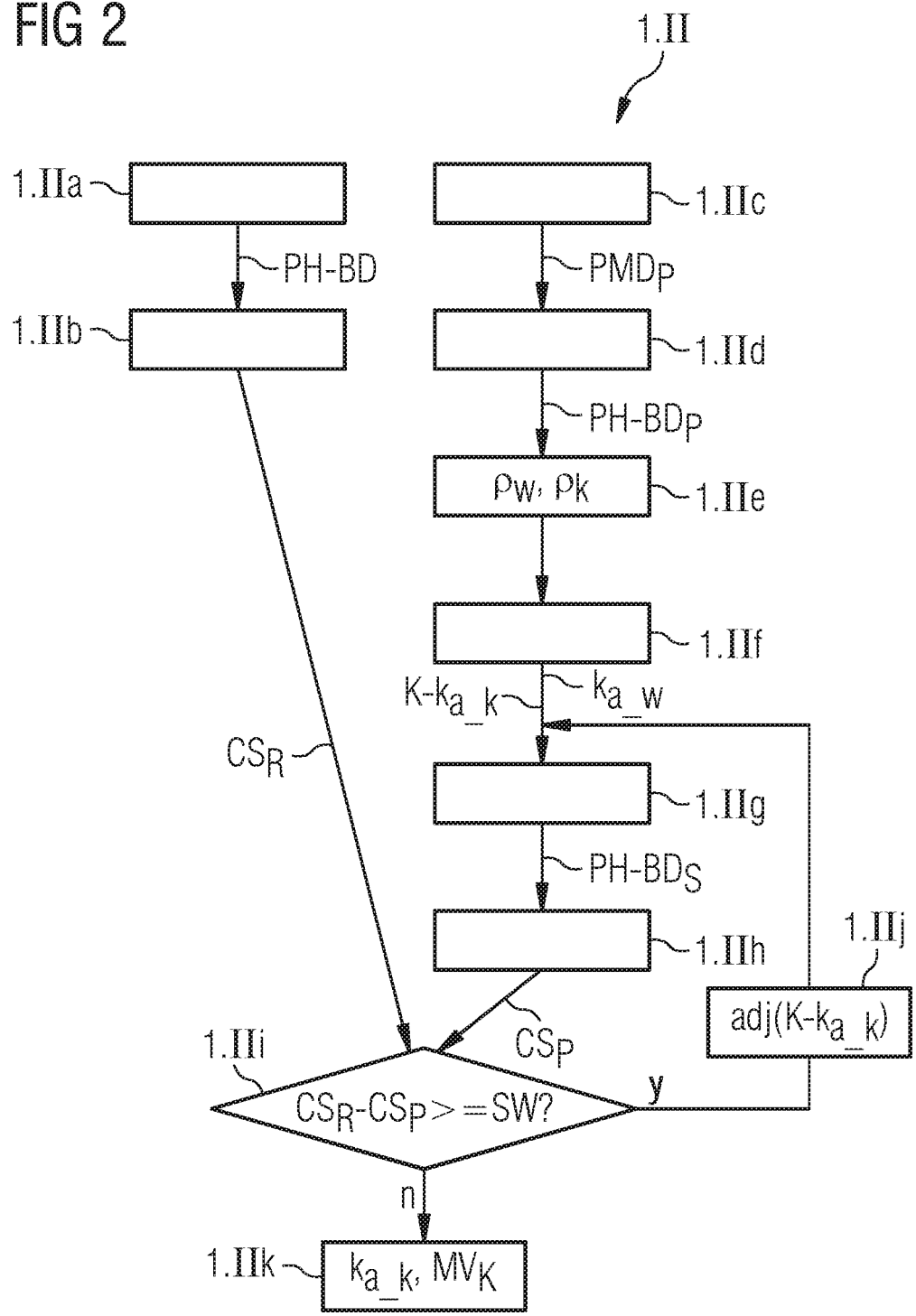

FIG. 2 illustrates the calibration process to be performed before the actual imaging of the patient within the context of Step 1.II. In Substep 1.IIa, first, phantom image data PH-BD from a reference phantom is acquired, which, for example, is already present in a database. The projection-measurement data assigned to the phantom image data PH-BD was acquired with reference CT-acquisition parameters CT-PA$_R$ with which a calcium score is also usually determined. For example, the reference CT-acquisition parameters CT-PA$_R$ can comprise a parameter value for an X-ray tube voltage of 120 kV. On the basis of the phantom image data PH-BD acquired, in Substep 1.IIb, a reference calcium score CS$_R$ is then calculated in the known manner, for example in accordance with Equations 1 to 3 described in the introduction to the description.

In addition, within the context of the calibration process, in Substep 1.IIc, projection-measurement data PMD$_P$ from the reference phantom is acquired with the aid of a CT system with patient-specific CT-acquisition parameters CT-AP$_P$ which are also to be used later during the CT imaging of the patient. In Substep 1.IId, then, phantom image data PH-BD$_P$ is reconstructed on the basis of the acquired projection-measurement data PMD$_P$ which is assigned to the patient-specific CT-acquisition parameters CT-AP$_P$. In Substep 1.IIe, basic material segmentation of the reconstructed image data PH-BD$_P$ is now performed. In this context, in this specific example embodiment, location-dependent density values $\rho_w$, $\rho_k$ are determined for the basic materials soft tissue and water.

Subsequently, in Step 1.IIf a candidate value K-$k_{a\_k}$ for the absorption coefficients $k_{a\_k}$ for the basic material calcium is calculated for the reference CT-acquisition parameters CT-AP$_R$. Parameters dependent upon the reference CT-acquisition parameters CT-AP$_R$ are included in the calculation, such as, for example, an X-ray energy spectrum which is correlated with the value of an X-ray tube voltage used, a prefilter used, an energy-dependent responsiveness of a CT-X-ray detector etc. It is usually possible for the value of the absorption coefficients $k_{a\_w}$ for the soft tissue to be left unchanged and then only the absorption coefficient $k_{a\_k}$ for calcium has to be further adapted. As already mentioned, this candidate value $K-k_{a\_k}$ is not necessarily correct as far as the calculation of a calcium score is concerned, and it is therefore compared with the reference calcium score $CS_R$ already determined in Substep 1.IIb.

To this end, first, in Substep 1.IIg synthetic phantom image data $PH-BD_S$ is calculated using the calculated absorption coefficients $k_{a\_w}$ for soft tissue and the candidate value $K-k_{a\_k}$ for the absorption coefficient for calcium. Then, in Step 1.IIg, a "synthetic" calcium score $CS_P$ is calculated on the basis of the synthetic phantom image data $PH-BD_S$ in accordance with Equations 1 to 3. This synthetic calcium score $CS_P$ is then compared in Substep 1.IIi with the reference calcium score $CS_R$. It is specifically checked whether a difference between the two scores $CS_P$, $CS_R$ exceeds a threshold value SW.

If this is the case, as indicated by "y" in FIG. 2, the method moves onto Substep 1.IIj with which there is an adjustment $adj(K-k_{a\_k})$ of the candidate value $K-k_{a\_k}$ for the absorption coefficient $k_{a\_k}$ for calcium. Then, the method returns to Step 1.IIg with which there is another calculation of synthetic phantom image data $PH-BD_S$ but now using the adjusted candidate value $K-k_{a\_k}$. In addition, in Substep 1.IIh once again a "synthetic" calcium score $CS_P$ is calculated and, in Step 1.Iii, this newly calculated "synthetic" calcium score $CS_P$ is compared with the reference calcium score $CS_R$. If, now, in this comparison a predetermined threshold value SW is fallen below, as indicated by "n" in FIG. 2, the method moves on to Substep 1.IIk and the current candidate value $K-k_{a-k}$ is adopted as a calibrated calcium-absorption coefficient $k_{a\_k}$ for the subsequent use of the now calibrated model method $MV_k$. This concludes the calibration of the model method $MV_k$. Then, the method shown in FIG. 1 is continued, as already described, with Step 1.III.

Figure 3:
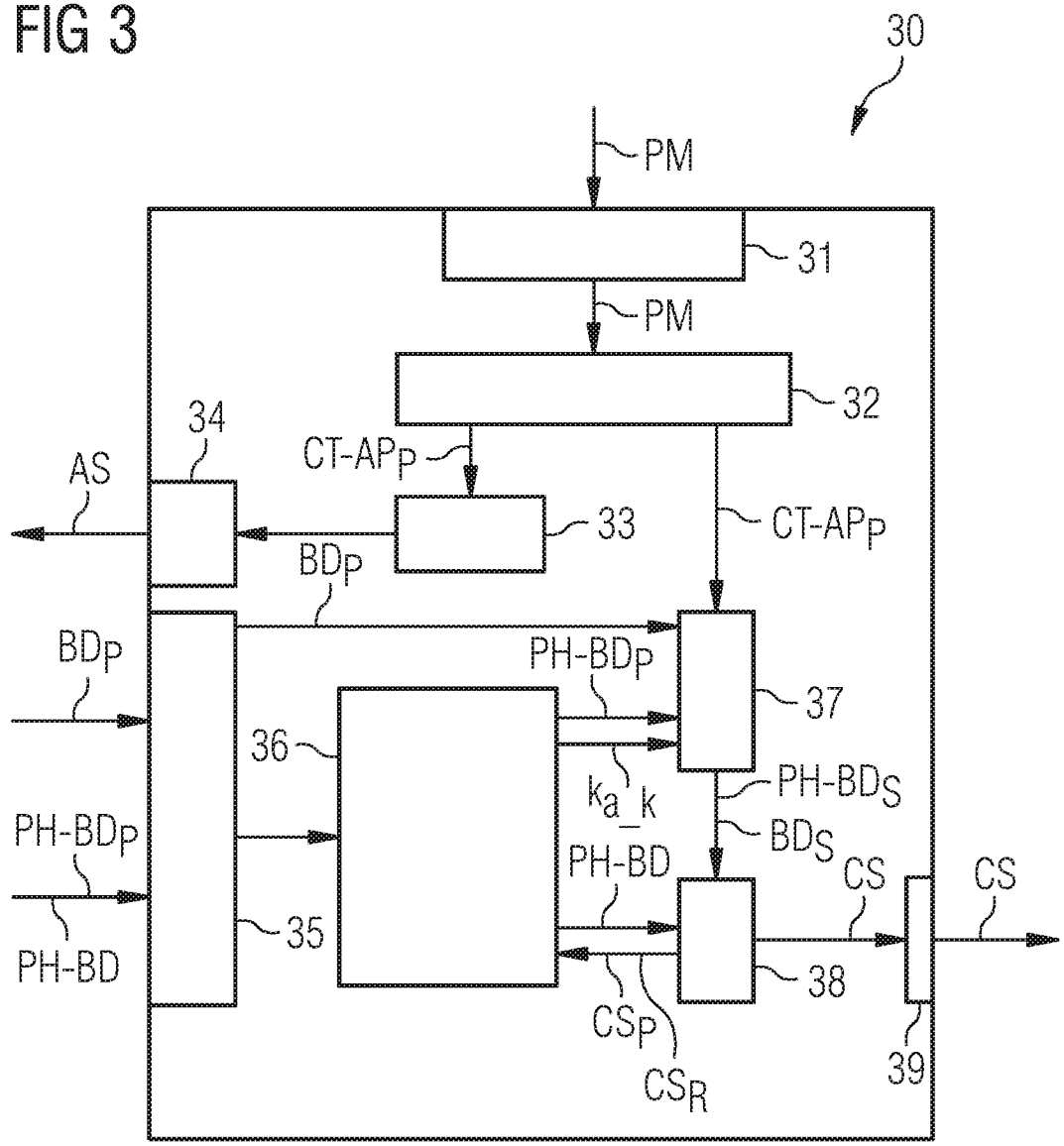

FIG. 3 shows a calcium-score-determining device 30 according to one example embodiment of the invention. Such a calcium-score-determining device 30 can, for example, be part of a control device of a CT system such as that shown in FIG. 6. The calcium-score-determining device 30 comprises an input interface 31. The input interface 31 can be used for the entry of patient-specific protocol parameters PM for example from a database or by a user for CT imaging. The patient-specific protocol parameters PM can, for example, be dimensions of the patient, an X-ray tube voltage to be used or the like. From the input interface 31, the patient-specific protocol parameters PM are sent to a parameter-defining unit 32. The parameter-defining unit 32 is used to define patient-specific CT-acquisition parameters $CT-AP_P$ on the basis of the received patient-specific protocol parameters PM. For example, a tube voltage to be used or a prefilter to be used can be defined in dependence on the patient's diameter or other patient-specific protocol parameters PM. The defined patient-specific CT-acquisition parameters $CT-AP_P$ are sent to an acquisition-control-signal-generating unit 33, which generates on the basis of the patient-specific CT-acquisition parameters $CT-AP_P$ a sequence of control signals or acquisition-control signals AS for CT imaging from a reference phantom for calibration, as described in connection with FIG. 2. The acquisition control signals AS are output via a signal output interface 34 to a control interface 24, shown in FIG. 6, to send acquisition-control signals AS to a CT scanning unit.

During said calibration process, now, with the aid of a scanning unit of a CT system (see FIG. 6), projection-measurement data is recorded from the reference phantom with the patient-specific CT-acquisition parameters $CT-AP_P$. On the basis of the projection-measurement data, phantom image data $PH-BD_P$ is reconstructed in the usual manner to form patient-specific CT-acquisition parameters $CT-AP_P$. The reconstructed phantom image data $PH-BD_P$ is sent via an image-data-input interface 35 to the calcium-score-determining device 30. From the image-data-input interface 35, the phantom image data $PH-BD_P$ is sent to a calibration unit 36, which is part of the calcium-score-determining device 30. In addition, the image-data-input interface 35 is also used to send reference phantom image data PH-BD to the calibration unit 36, which for example originate from a database or are recorded directly from the phantom with reference CT-acquisition parameters $CT-AP_R$, also called standard CT-acquisition parameters. The values of the reference CT-acquisition parameters $CT-AP_R$ correspond to the values of the standard CT-acquisition parameters, for which a calcium score is defined and with which CT imaging would conventionally be performed in order to determine such a calcium score.

The calibration unit 36 is used to calibrate material parameters $k_{a\_k}$ for a model method. As explained in connection with FIG. 1 and FIG. 2, the model method is used to generate synthetic image data $BD_S$ for virtual CT-acquisition parameters. In the application according to the invention of this model method, the virtual CT-acquisition parameters are the reference CT-acquisition parameters $CT-AP_R$ with which a calcium score is conventionally determined. During the calibration process, the reference phantom image data PH-BD recorded with reference CT-acquisition parameters $CT-AP_R$ is used as comparative data and the calibration is performed such that a calcium score $CS_P$ determined on the basis of the synthetic phantom image data $PH-BD_S$ corresponds to a calcium score $CS_R$ determined on the basis of the reference phantom image data PH-BD recorded with reference CT-acquisition parameters $CT-AP_R$. To this end, the phantom image data $PH-BD_P$ for patient-specific CT-acquisition parameters $CT-AP_P$ is sent to a synthesis unit 37. The synthesis unit 37 generates on the basis of the phantom image data $PH-BD_P$ synthetic phantom image data $PH-BD_S$ for the known reference CT-acquisition parameters $CT-AP_R$. Then, the synthetic phantom image data $PH-BD_S$ is sent to a calcium score-determining unit 38 which calculates a calcium score $CS_P$ on the basis of the synthetic phantom image data $PH-BD_S$. This calcium score $CS_P$ is compared by the calibration unit 36 with a calcium score $CS_R$ determined by the calcium score-determining unit 38 using the reference phantom image data PH-BD or which was already known in advance.

If the calibration unit 36 now determines that the calcium score $CS_P$ for the synthetic phantom image data $PH-BD_S$ deviates too greatly from the reference value $CS_R$, candidate values for the material parameters, for example a candidate value $K-k_{a\_k}$ for the absorption coefficients $k_{a\_k}$ for the material calcium, are modified. Then, the synthesis unit 37 regenerates synthetic phantom image data $PH-BD_s$ but now with the modified candidate value $K-k_{a\_k}$ for the absorption coefficients $k_{a\_k}$ for calcium. On the basis of the new synthetic phantom image data $PH-BD_s$, the calcium score-determining unit 38 now recalculates a calcium score $CS_P$ which the calibration unit 36 again compares with the reference calcium score $CS_R$. If the two are now identical or do not deviate from each other by more than a predetermined threshold value, the associated values $k_{a\_k}$, $k_{a\_w}$ for the material parameters can be sent to the synthesis unit 37 and stored there.

This is followed by the actual CT imaging of a region of interest, for example the heart of the patient with the defined patient-specific CT-acquisition parameters CT-AP$_P$. The image data BD$_P$ generated in this context is also sent via the image-data-input interface 35 to the calcium-score-determining device 30. There, the image data BD$_P$ is forwarded to the synthesis unit 37, which generates synthetic image data BD$_S$ on the basis of the image data BD$_P$ using the model method MV$_k$ adapted with the calibrated material parameters $k_{a\_k}$, $k_{a\_w}$. The synthetic image data BD$_S$ is then transferred to the calcium score-determining unit 38 which calculates a calcium score CS on the basis thereof. The calcium score CS is output via an output interface 39 to a data storage unit or for depiction on a display.

Figure 4:
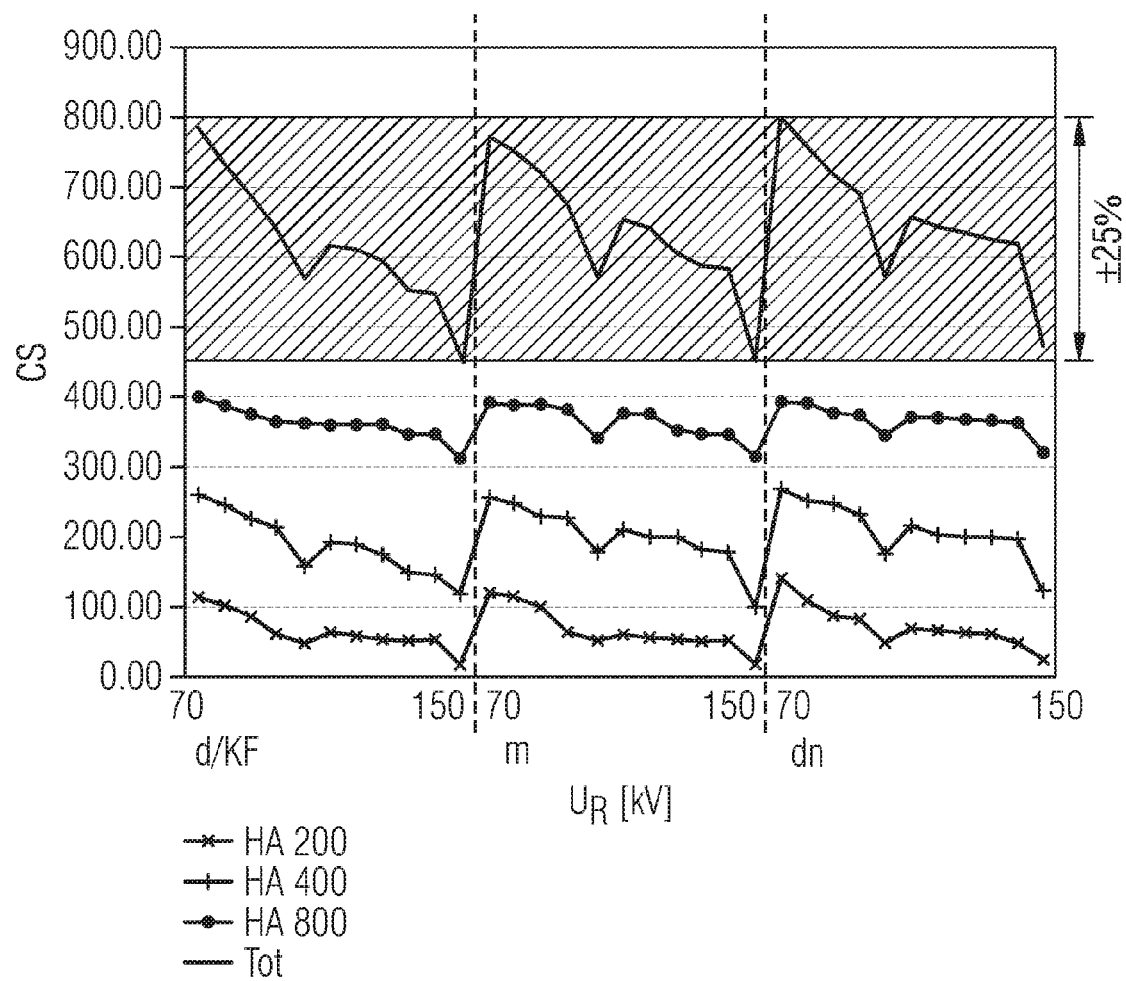

FIG. 4 shows a graph in which an Agatston score CS is depicted in dependence on different CT-acquisition parameters. I.e., for the determination of the Agatston Scores CS, first CT-image data with patient-specific acquisition parameters CT-AP$_P$ is generated. In the graph shown in FIG. 4, these patient-specific acquisition parameters CT-AP$_P$ comprise the X-ray tube voltage U$_R$, which for different recordings, adopt different values of from 70 to 150 kV. In this context, the "patients" used were patient-like phantoms with three different dimensions intended to simulate a 'fat' patient d, a normal patient m and a thin patient dn. In addition, a prefilter KF was used for the CT scan of the 'fat' "patient" d. In FIG. 4, the different "patients" d, m, dn are each assigned to different columns of the graph, which are separated from one another by dashed lines.

The phantoms also comprise different regions with different calcium concentration or concentrations of hydroxylapatite HA correlated therewith, namely 200 mg/cm$^3$, 400 mg/cm$^3$ and 800 mg/cm$^3$, identified in the graph as HA 200, HA 400 and HA 800. In the graph in FIG. 4, the different regions with different calcium concentrations are each marked with Agatston Scores. In addition, a combined Agatston score (in the legend symbolized with the abbreviation "Tot") covering all the regions of the "patient" is marked on the group. As can be identified in FIG. 4, the Agatston score varies in particular in dependence on the X-ray tube voltage U$_R$ by 25%, and to a lesser extent in dependence on the patient's size and the prefiltering.

In order to obtain a correct Agatston score, it is conventionally necessary for there to be a restriction to standard conditions, in particular an X-ray tube voltage of 120 kV. However, even with standardized CT-acquisition parameters, the values for the Agatston score can vary by 6% with one and the same patient.

Figure 5:
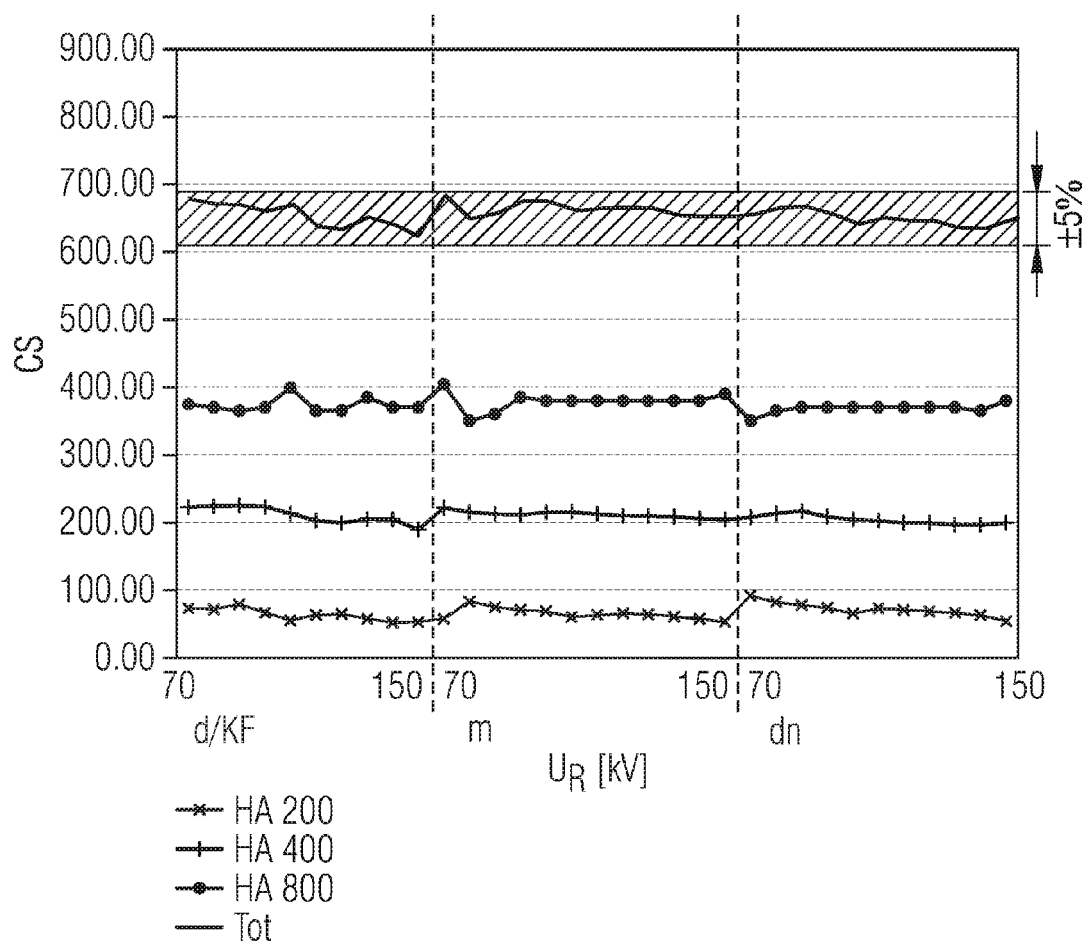

For purposes of comparison, FIG. 5 shows a graph also illustrating values for an Agatston score in dependence on CT-acquisition parameters comprising the X-ray tube voltage UR, the patient thickness and the prefiltering. However, unlike FIG. 4, in this case, the values for the Agatston score were obtained with the method described in connection with FIG. 1 and FIG. 2.

The graph shown in FIG. 5 also uses the patient-like phantom with different regions with different calcium concentrations used for the determination of the Agatston score in FIG. 4. To this end, in the legend in FIG. 5, concentrations of hydroxylapatite HA, namely 200 mg/cm$^3$, 400 mg/cm$^3$ and 800 mg/cm$^3$ correlating thereto are identified as HA 200, HA 400 and HA 800. In the graph in FIG. 5, the different regions with different calcium concentrations are each marked with Agatston scores. The graph also shows a combined Agatston score (symbolized in the legend with the abbreviation "Tot") covering all the areas of the "patient".

As can be identified in FIG. 5, the Agatston score CS varies much less, above all in dependence on the X-ray tube voltage U$_R$ used, namely only by about 5%. This shows the superiority of the procedure according to the invention, which in particular permits a variation of the X-ray tube voltage U$_R$ during the CT imaging for the determination of an Agatston score CS.

Figure 6:
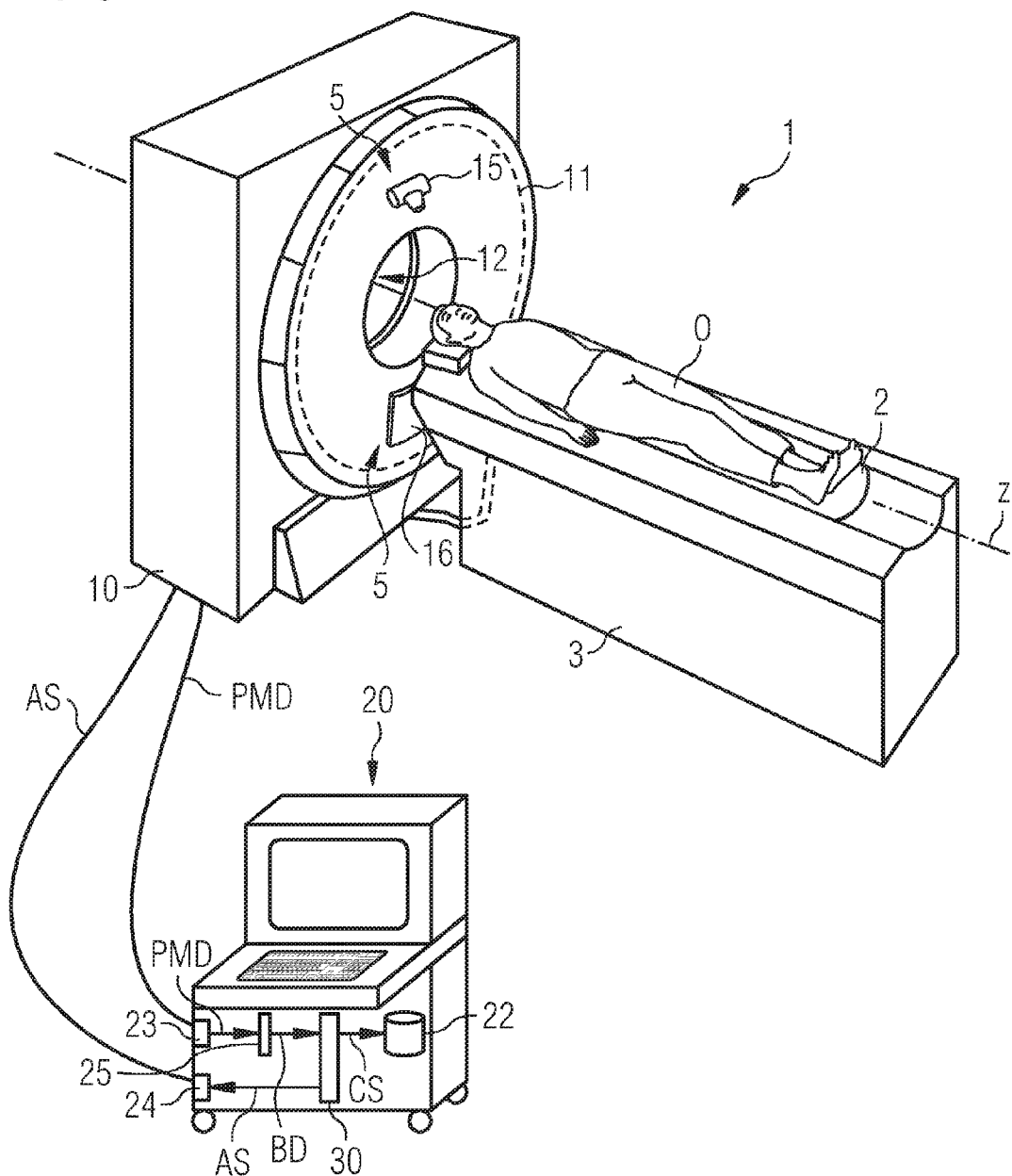

FIG. 6 shows a computed tomography system 1 according to one example embodiment of the invention, which also comprises a calcium-score-determining device 30 according to one example embodiment corresponding to the arrangement shown in FIG. 3. In this context, the CT system 1 essentially includes a customary scanner 10 in which a projection-data-acquisition unit 5 with a detector 16 and X-ray source 15 oppositely disposed to the detector 16 on a gantry 11 rotates about a scanning chamber 12.

In front of the scanner 10, there is a patient support device 3 or a patient table 3 the upper part 2 of which can be pushed with the patient O located thereupon toward the scanner 10 in order to move the patient O through the scanning chamber 12 relative to the detector system 16. The scanner 10 and the patient table 3 are controlled by a control device 20 from which acquisition control signals AS are sent via a customary control interface 24 in order to control the entire system in accordance with prespecified scanning protocols in the conventional manner. In the case of spiral acquisition, a movement of the patient O along the z-direction, which corresponds to the system z lengthwise through the measuring chamber 12, and the simultaneous rotation of the X-ray source 15 results in a helical path for the X-ray source 15 relative to the patient O during the scan. In this context, the detector 16 always moves in parallel with the X-ray source 15 in order to acquire projection-measurement data PMD which is then used for the reconstruction of volume and/or slice image data.

It is also possible to perform a sequential scanning method with which a fixed position in the z-direction is approached and then, during a rotation, a partial rotation or several rotations at the z-position in question, the necessary projection-measurement data PMD is obtained in order to reconstruct a sectional view at this z-position or to reconstruct image data BD from the projection data of several z-positions. The method according to the invention illustrated in FIG. 1 and FIG. 2 can in principle also be used on other CT systems, for example, with a plurality of X-ray sources and/or detectors and/or with a detector forming a complete ring.

The projection-measurement data PMD acquired by the detector 16 (hereinafter also called raw data PMD) is sent via a raw-data interface 23, also called a raw-data-acquisition unit, to the control device 20. This raw data PMD is then, optionally after suitable preprocessing (e.g. filtering and/or beam hardening correction), further processed in an image-reconstruction unit 25, which, in this example embodiment, is implemented in the control device 20 in the form of software on a processor. This image-reconstruction unit 25 reconstructs image data BD on the basis of the raw data PMD with the aid of a reconstruction method. The reconstruction method can, for example, be a reconstruction method based on filtered back projection. The reconstructed image data, be it phantom image data PH-BD, PH-BD$_P$ or image data BD$_P$ generated with patient-specific CT-acquisition parameters CT-AP$_P$ (see FIG. 3), is processed by a calcium-score-determining device 30 so that, in the case of phantom image data PH-BD, PH-BD$_P$, it can be used in the manner shown in FIG. 2 for the calibration of a model method for image data synthesis, or in the case of the image data BD$_P$ generated with patient-specific CT-acquisition parameters CT-AP$_P$ for the determination of a calcium score CS, in particular an Agatston score.

The values CS determined are stored in a memory 22 of the control device 20 and/or output in the customary manner on the screen of the control device 20. It can also be fed via an interface, which is not shown in FIG. 6, into a network connected to the computed tomography system 1, for example a radiology information system (RIS), and stored in an mass memory which can be accessed there or output on a printers connected thereto. In this way, the data can be further processed as desired and then stored or output.

Finally, reference is made once again to the fact that the above-described method and the described calcium-scored-determining device 30 and the described computed tomography system 1 are only preferred example embodiments of the invention and that the invention can be varied by the person skilled in the art without departing from the scope of the invention insofar as this is specified by the claims. Moreover, it is pointed out for the sake of completeness, that the use of the indefinite article "a", "an" does not exclude the presence of a plurality of the relevant features. Likewise, the term "unit" does not exclude the possibility that this may consist of a plurality of components which may also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a calcium score for a patient to be examined with the aid of a CT system, comprising:
    defining patient-specific CT-acquisition parameters;
    calibrating material parameters for a model method with which synthetic image data for virtual CT-acquisition parameters are generated, wherein the calibrating is performed using phantom image data recorded with reference CT-acquisition parameters such that a calcium score determined on the basis of synthetic phantom image data corresponds to a calcium score determined on the basis of the phantom image data recorded with reference CT-acquisition parameters;
    acquiring CT-projection-measurement data for a region of interest using the patient-specific CT-acquisition parameters;
    generating synthetic image data on the basis of the acquired CT-projection-measurement data using a model method adapted with the calibrated material parameters; and
    determining the calcium score on the basis of the generated synthetic image data.

2. The method of claim 1, wherein the generating of the synthetic image data using the model method adapted comprises:
    reconstructing image data on the basis of the X-ray projection-measurement data acquired using the patient-specific CT-acquisition parameters;
    segmenting the image data according to material properties; and
    determining of synthetic image data for the reference CT-acquisition parameters on the basis of the segmentation and using the calibrated material parameters.

3. The method of claim 1, wherein the patient-specific CT-acquisition parameters are defined taking account of the dose efficiency for the depiction of the calcium-soft tissue contrast.

4. The method of claim 1, wherein an X-ray tube voltage assigned to a patient-specific X-ray energy spectrum is defined as a patient-specific CT-acquisition parameter.

5. The method of claim 4, wherein the patient-specific X-ray energy spectrum is selected such that a desired dose efficiency for the depiction of the calcium-soft tissue contrast is achieved.

6. The method of claim 4, wherein the patient-specific X-ray energy spectrum is defined in dependence on at least one of dimensions of the patient and an attenuation of the X-rays in the patient.

7. The method of claim 1, wherein the patient-specific CT-acquisition parameters comprise a patient-specific X-ray energy spectrum and wherein the reference CT-acquisition parameters comprise a reference X-ray energy spectrum.

8. The method of claim 2, wherein the segmentation according to material properties comprises one of the following:
    basic material segmentation,
    photo/Compton effect segmentation, and
    density-charge number segmentation.

9. The method of claim 1, wherein the material parameters to be defined during the calibrating comprise the absorption coefficients of the basic materials.

10. The method of claim 9, wherein the synthetic image data comprise monoenergetic image data and in the calibrating, the absorption coefficients of the basic materials are defined such that a calcium score determined at an X-ray energy corresponding to the patient-specific acquisition parameters corresponds to a calcium score determined at a reference X-ray energy corresponding to the reference CT-acquisition parameters.

11. The method of claim 1, wherein the calibrating is performed with the aid of phantom image data generated at least one of
    by displaying a reference phantom with a known calcium score or by displaying an anthropomorphic phantom; and
    by taking account of patient data.

12. A non-transitory computer program product including a computer program, directly loadable into a storage device of a computer tomography system, including program sections for carrying out the method of claim 1 when the computer program is executed in a control device of the computer tomography system.

13. A non-transitory computer-readable medium including program sections, readable and executable by a computing unit, to carry out the method of claim 1 when the program sections are executed by the computing unit.

14. The method of claim 1, wherein the acquiring of the region of interest is a heart region of the patient.

15. The method of claim 2, wherein the patient-specific CT-acquisition parameters are defined taking account of the dose efficiency for the depiction of the calcium-soft tissue contrast.

16. The method of claim 2, wherein an X-ray tube voltage assigned to a patient-specific X-ray energy spectrum is defined as a patient-specific CT-acquisition parameter.

17. The method of claim 16, wherein the patient-specific X-ray energy spectrum is selected such that a desired dose efficiency for the depiction of the calcium-soft tissue contrast is achieved.

18. The method of claim 2, wherein the patient-specific CT-acquisition parameters comprise a patient-specific X-ray energy spectrum and wherein the reference CT-acquisition parameters comprise a reference X-ray energy spectrum.

19. The method of claim 2, wherein the material parameters to be defined during the calibrating comprise the absorption coefficients of the basic materials.

20. The method of claim 19, wherein the synthetic image data comprise monoenergetic image data and in the calibrating, the absorption coefficients of the basic materials are defined such that a calcium score determined at an X-ray energy corresponding to the patient-specific acquisition parameters corresponds to a calcium score determined at a reference X-ray energy corresponding to the reference CT-acquisition parameters.

21. A calcium-score-determining device to determine a calcium score for a patient to be examined with the aid of a CT system, comprising:
 a parameter-defining device to define patient-specific CT-acquisition parameters;
 a calibration unit to calibrate material parameters for a model method with which synthetic image data for virtual CT-acquisition parameters are generated, the calibration being performed using phantom image data recorded with reference CT-acquisition parameters such that a calcium score determined on the basis of synthetic phantom image data corresponds to a calcium score determined on the basis of the phantom image data recorded with reference CT-acquisition parameters;
 an acquisition-control-signal-generating unit to generate acquisition-control signals for the acquisition of CT-projection-measurement data for a region of interest using the patient-specific CT-acquisition parameters;
 a synthesis unit to generate synthetic image data on the basis of the acquired CT-projection-measurement data using a model method adapted with the calibrated material parameters; and
 a calcium score-determining unit to determine the calcium score on the basis of the synthetic image data.

22. A computed tomography system comprising:
 a scanning unit to acquire a region of interest of an object under examination;
 a control device to control the scanning unit; and
 the calcium-score-determining device of claim 21.

* * * * *